(12) United States Patent
Åkerblom (10) Patent No.: US 10,161,894 B2
(45) Date of Patent: Dec. 25, 2018

(54) DEVICE FOR DETECTING PROFILE IN REFINER AND METHOD THEREFORE

(71) Applicant: Daprox AB, Kungens Kurva (SE)

(72) Inventor: Bengt Åkerblom, Vårby (SE)

(73) Assignee: Daprox AB, Kugens Kurva (SE)

( * ) Notice: Subject to any disclaimer, the term of this patent is extended or adjusted under 35 U.S.C. 154(b) by 0 days.

(21) Appl. No.: 15/034,140

(22) PCT Filed: Oct. 13, 2014

(86) PCT No.: PCT/SE2014/051209
§ 371 (c)(1),
(2) Date: May 3, 2016

(87) PCT Pub. No.: WO2015/065268
PCT Pub. Date: May 7, 2015

(65) Prior Publication Data
US 2016/0258893 A1     Sep. 8, 2016

(30) Foreign Application Priority Data
Nov. 4, 2013 (SE) ...................... 1351299

(51) Int. Cl.
*G01N 27/04* (2006.01)
*G01N 33/40* (2006.01)
(Continued)

(52) U.S. Cl.
CPC ............. *G01N 27/045* (2013.01); *D21D 1/30* (2013.01); *G01N 27/04* (2013.01); *G01N 33/34* (2013.01); *G01N 33/343* (2013.01); *G01N 33/40* (2013.01)

(58) Field of Classification Search
CPC ...... G01N 27/045; G01N 33/40; G01N 33/34; G01N 27/04; G01N 33/343; D21D 1/30
See application file for complete search history.

(56) References Cited

U.S. PATENT DOCUMENTS

| 4,454,991 A | 6/1984 | Brenholdt |
| 4,624,742 A * | 11/1986 | Klein ................. D21C 9/06 162/263 |

(Continued)

FOREIGN PATENT DOCUMENTS

| EP | 1 132 518 A2 | 9/2001 |
| EP | 1 132 518 A3 | 1/2002 |

(Continued)

OTHER PUBLICATIONS

International Search Report for PCT/SE2014/051209 dated May 2, 2015.

(Continued)

*Primary Examiner* — Huy Q Phan
*Assistant Examiner* — Zannatul Ferdous
(74) *Attorney, Agent, or Firm* — Knobbe Martens Olson & Bear, LLP (57) ABSTRACT

The invention regards a measuring device, comprising a conductor body (7), for detecting the degree of fiber concentration and/or steam point (SP) of a fiber pad (33) being pulped, during use of the device (3), in a grinding gap (15) between refiner discs (11, 13) of a refiner (1). The conductor body (7) exhibits a first electric contact surface (17) adapted to provide electrical contact with a second electric contact surface (19) for transferring an electric current via the fiber pad (33) material. The invention also regards a method for detecting the degree of fiber concentration and/or steam point (SP) of a fiber pad (33). The method comprises the steps of mounting of the conductor body (7) to one of the refiner discs (13), grinding the fiber pad (33) material between the refiner discs (11, 13), detecting alteration of the conductivity and/or electrical resistivity of the fiber pad (33) material, and adjusting inflow of water and/or fiber material from said detected alteration.

8 Claims, 4 Drawing Sheets

(51) Int. Cl.
*G01N 33/34* (2006.01)
*D21D 1/30* (2006.01)

(56) References Cited

U.S. PATENT DOCUMENTS

| | | | |
|---|---|---|---|
| 5,410,129 A * | 4/1995 | Kersten | A47J 27/62 |
| | | | 219/497 |
| 2003/0004676 A1 | 1/2003 | Johansson | |
| 2005/0211809 A1 | 9/2005 | Lutz | |
| 2007/0164757 A1* | 7/2007 | Akerblom | G01N 33/343 |
| | | | 324/663 |
| 2013/0067992 A1* | 3/2013 | Sinha | G01F 1/666 |
| | | | 73/24.04 |

FOREIGN PATENT DOCUMENTS

| | | |
|---|---|---|
| WO | WO 01/76756 A2 | 10/2001 |
| WO | WO 2005/083408 A1 | 9/2005 |

OTHER PUBLICATIONS

Extended European Search Report received in 14856988.2, dated Apr. 21, 2017.

* cited by examiner

DEVICE FOR DETECTING PROFILE IN REFINER AND METHOD THEREFORE

CROSS REFERENCE TO RELATED APPLICATIONS

This application is a U.S. National Phase Application of PCT International Application Number PCT/SE2014/051209, filed on Oct. 13, 2014, designating the United States of America and published in the English language, which is an International Application of and claims the benefit of priority to Swedish Patent Application No. 1351299-1, filed on Nov. 4, 2013. The disclosures of the above-referenced applications are hereby expressly incorporated by reference in their entireties.

TECHNICAL FIELD

The present invention relates to a measuring device according to the preamble of claim 1 and to a method.

The invention regards refiners and pulp producing plants. It is associated with industry for making paper, fiber board's etc. It also relates to Research and Development projects having an object to improve energy efficiency in Thermo Mechanical Pulp TMP plants or similar.

BACKGROUND ART

There have been several attempts to improve the measurement of fiber concentration in a so called refiner zone of a fiber pad distribution being processed between mill plates (discs) of a refiner. New measurement techniques have been developed to keep the quality of the pulp as consistent as possible. Sensor means are mounted in refiners for measure of fiber concentration in the fiber pad. Paper making industry using refiners has interest in saving energy and there is a desire to balance energy consumption and fiber material refining process using such sensor means. However, there are still no efficient way to measure fiber concentration and steam point between refiner plates for reaching a high quality production at the same time energy saving process. In research work so called sensor-rich systems are used for estimation of fiber consistency. However, such systems are bulky and require complex software applications executing data from temperature sensors, motor loads, dilution water feeding rate, inlet temperature and pressure, material properties etc. The use of temperature data is hazardous since the temperature per se does not indicate the refiner pad consistency and fiber concentration.

The applicant of this application also presented one way to overcome above problems according to an alternative solution in the document WO 2005/083408. It reveals that the magnitude of the movement of an impedance sensor body and the change of the impedance over said movement can be used for determination of a value for a dielectric constant of the refiner pad. Software is used for determination of the fiber concentration. A correlation between dielectric constant and degree of fiber concentration is utilized for determination of the fiber concentration. The device disclosed in WO 2005/083408 is of high technical value to the field. However, there is a desire to develop and simplify known devices for determination of the fiber concentration of a refiner pad within the refiner zone and for determination of the steam point of the refiner in-between the plates.

It is desirable save further energy in the paper making industry.

It is desirable to produce a high quality pulp by proper measurement of fiber concentration in the refiner pad.

It is desirable to detect in which region of the refiner plate gap the steam point prevails.

The invention is provided for solving a problem defined by the enclosed independent claims and related to the technical field.

SUMMARY OF THE INVENTION

This has been achieved by the measuring device being defined in the introduction and being characterized by the features of the characterizing part of claim 1.

In such way is achieved that on-line measurement is achieved within a zone between the refiner discs, preferably adjacent a grind gap sensor of the type AGS (adjustable gap sensor), in an efficient way.

It will thus be possible to control the refiner performance from detected fiber concentration and/or steam point. An user of the refiner can thus cost-effective perform automatic recalibrations during production and continuously correlate water amount inflow in-between the refiner discs, thereby controlling the position of the steam point in radial direction of the refiner discs. Such continuous measurement implied improved production rate as well.

The position of the steam point is important for cost-effective reaching the production of proper pulp quality and at the same time not unnecessary overloading of the refiner, which in turn involves high power consumption.

The area A of the first electric contact surface, the length L of the grinding gap embodying the fiber pad, i.e. the distance between the refiner discs, and the actual electrical resistivity p of the fiber pad material will determine the electrical resistance R, which being measured continuously for detecting the alteration of the electrical resistivity of the fiber pad, and thereby the actual fiber concentration and/or the position of the steam point. The formula is $$R = \frac{\rho L}{A}$$

where R is resistance, p is resistivity, L is the gap between the refiner discs and A is the area of the first electric contact surface. By means of the device, such detection of variations in electrical resistivity is possible. This improves refiner performance. The detection of variations correlates to altered fiber concentration. Adjustment of e.g. the added amount of water to the fiber pad is performed for altering the fiber concentration.

Preferably, the device comprises a second type of conductor bodies, each including a first electric contact surface and the surfaces being positioned in radial direction of the discs for measuring a steam point profile.

Thereby is achieved that the measured conductivity and/or electrical resistivity over the refiner disc radial direction, partly or entirely, can be used by a control unit to execute and display a curve profile indicating the actual changes of the electrical material property of the fiber pad during production. The varying of electrical material properties of the fiber pad generates an indication pointing at to which position the steam point moves over the refiner disc grinding gap in the radial direction. A certain set value for conductivity and/or electrical resistivity is determined to indicate for example the steam point. The actual value of conductivity and/or electrical resistivity is measured for each conductor body for providing an actual curve profile. This actual curve profile being matched by the control unit to correlate with the set values determining a set curve profile.

Suitably, the device further comprises a control unit adapted to detect alteration of the electrical resistivity and/or conductivity of the material by measuring said electric current.

In such way is achieved that a curve profile representing the fiber pad material properties can be displayed on a computer screen.

Preferably, the second electric contact surface is formed by the rotor refiner disc.

In such way is achieved that the rotating rotor refiner disc per se can be used as a component for the device. Each connection or earth wire has to be connected to the rotor refiner disc and can be made via its axis. Preferably, a slip contact is used for contacting the refiner disc. The current is fed between the conductor body/bodies and the rotor refiner disc. This also implies that the devices conductor body/bodies can be mounted in the stator refiner disc. The stator refiner disc is stationary and this simplifies the operation of the conductor body/bodies, for example in service and mounting.

Suitably the device comprises conductor body, which are connected in series with a respective series resonance circuit SRC being individually adapted to give free passage for the electric current to a certain frequency.

In such a way the number of lead wires coming from the circuit is reduced. This is made by earmarking each individual conductor body by arranging each one in series with a specific series resonance circuit (the abbreviation of which used herein SCR) having a certain frequency at which the current is given passage. By sweeping the frequency of the current in the circuit, the specific electrical resistivity and/or conductivity of the fiber pad in different positions along the radii of the refiner disc can be measured. By injecting various frequencies of the current, it is thus possible to achieve individual signatures of each conductor body. The rate of changing the direction of the AC defines the frequency. The frequency is suitably provided by a signal generator associated with an AC power source (transformer driver). An individual signature is made by earmarking each conductor body by coupling the latter to the specific SRC having a different resonance frequency that the others due to its certain RLC (resistance of e.g. lead wire, inductance, and capacitance). The earmarked conductor body is thus connected in series with the certain SRC (which is adapted to give passage of current for a specific frequency) and is used to respond selectively to signals of the specific frequency. The SRC comprises a lead wire, inductor, capacitor connected in series. Thus, by injecting various frequencies of the current is it possible to achieve industrial signatures of each conductor body position.

Preferably, the signal generator is adapted to generate a frequency sweep from 10 kHz till 200 kHz to the circuit. The signal generator alternatively generates electrical output waveforms over a preferable range of frequencies (5-250 kHz). The power source is preferably controlled by a frequency sweep controller as to execute the frequency sweep. The frequency of the driving voltage can preferably be swept from a predetermined upper frequency 300 kHz to a predetermined lower frequency 0.5 kHz by means of a sweep generator connected to the power source. Furthermore, the signal generator preferably includes a function of automatically and repetitively sweeping the frequency of the output waveforms by means of a voltage controlled oscillator between two defined limits. Thus, by sweeping frequency of the current over a specific frequency range for example 10-200 kHz) covering the different individually set resonance frequencies of the various SRCs (in this example; a first SRC is set to 10 kHz, a second set to 20 kHz, a third set to 30 kHz, etc, and up to 200 kHz for the last SRC.

Suitably, the conductor bodies are positioned side by side along a straight line in an elongated body, wherein the first electric contact surfaces are coplanar with the grinding surface of the refiner disc in which the elongated body is mounted.

In such way is achieved that also a simplified handling for service personnel is provided. The elongated body preferably also encompasses and adjustable gap sensor as well. In such way is provided a multi-functional sensor which is adapted for cost-effective production of pulp material.

Preferably, the conductor body is part of an adjustable gap sensor.

Thereby a compact sensor device is achieved.

In such way is achieved that the steam point and or the concentration of the fiber pulp material can be detected. It will thus be possible to control the refiner performance from the detection. The position of the steam point is very important for providing cost-effective production of proper pulp quality.

Preferably, the area A of the first electric contact surface, the length L of the grinding gap embodying the fiber pad, i.e. the distance between the refiner discs, and the actual electrical resistivity $\rho$ of the fiber pad material will determine the electrical resistance R, which being measured continuously for detecting the alteration of the electrical resistivity of the fiber pad, and thereby the actual fiber concentration and/or the position of the steam point.

Suitably, the area A of the first electric contact surface, the length L of the grinding gap embodying the fiber pad, i.e. the distance between the refiner discs, and the actual electrical conductivity of the fiber pad material will determine the electrical conductance, which being measured continuously for detecting the alteration of the conductance of the fiber pad, and thereby the actual fiber concentration and/or position of the steam point.

Prefereably, the step of detecting the alteration of the conductivity and/or electrical resistivity provides the detecting of the steam point of the fiber pad material.

In such way is achieved that, for example, a substantial alteration of the conductivity and/or electrical resistivity of the fiber pad material involves that the material transfers from liquid state to gaseous state or vice versa. This means that such detection can be used for determining the state of the fiber pad. If the steam point is determined to prevail at a specific radius point of the refiner disc and wherein this specific radius point corresponds to the position of the conductor body, and a substantial alteration of the conductivity and/or electrical resistivity of the fiber pad material is due, this is detected by the device feeding data to a control unit regulating the proportions of substances making the fiber pad material.

Suitably, the step of detecting the alteration of the electrical resistivity is made in radial direction of the discs.

In such way is achieved that a curve profile representing the fiber pad material properties can be displayed on a computer screen.

Preferably, there are arranged a plurality of conductor bodies along a straight line following the direction of the radius of the refiner disc. The conductor bodies are elongated and each conductor body comprises an end surface serving as the first electric contact surface. The conductor bodies are arranged in the refiner disc in such way that the first electric contact also follow said straight line. Of course, the line can be curved as well.

Suitably, each body is subjected to an electrical current and the opposite refiner disc grinding surface acts as a second electric contact surface whereby the current, applied to each conductor body, is fed between the conductor body and the refiner disc via the fiber pad material. The fiber pad material thus serves as a conductor by itself and exhibits a certain conductivity/electrical resistivity depending upon the actual fiber concentration and/or the actual moisture content and from what the actual gaseous or liquid state of the water content or other gaseous phase of the fiber pad material.

Preferably, the step of detecting the alteration of the electrical resistivity is made by means of a set of conductor bodies, which are connected in series with a respective series resonance circuit SRC, the series connection are connected together in parallel to a power source, wherein each series resonance circuit SRC being individually adapted to give free passage for said electric current to a certain frequency.

In such way is achieved that the device can be made with a minor number of cables which exit the device. This promotes an easy handling of the device.

Suitably, a power source for providing the electric current is an AC voltage power unit for generating an AC current over a transformer comprising a secondary winding of the device.

Thereby the current used for refiner disc gap sensors and other adjustable gas sensors can be used also for determining the fiber concentration and/or steam point of the fiber pad material.

Preferably, a power source is provided with a frequency generator means for generating a range of varying frequencies of said electric current.

BRIEF DESCRIPTION OF THE DRAWINGS

The present invention will now be described by way of examples with references to the accompanying schematic drawings, of which.

DETAILED DESCRIPTION

Hereinafter, embodiments of the present invention will be described in detail with reference to the accompanying drawings, wherein for the sake of clarity and understanding of the invention some details of no importance are deleted from the drawings.

Figure 1:
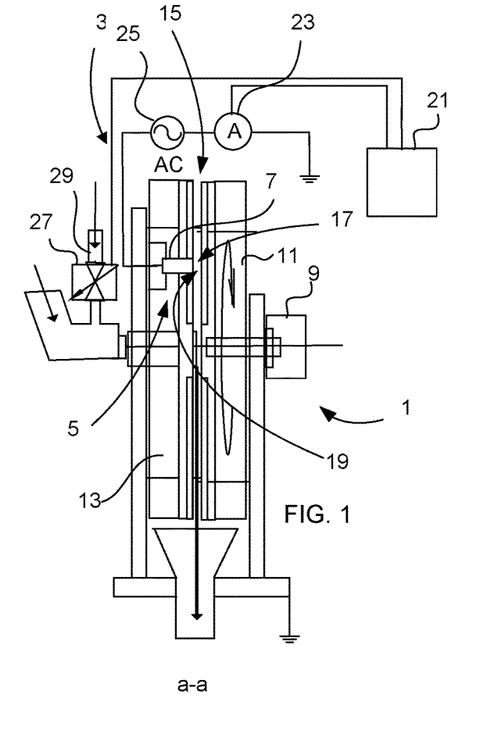
FIG. 1 illustrates a refiner comprising a measuring device according to one aspect of the invention.

FIG. 1 illustrates a refiner 1 arranged for pulping a fiber pad into a pulp. The refiner 1 comprises a measuring device 3, comprising a sensor probe 5 including a conductor body 7 adapted to conduct an electric AC current. A motor 9 drives a rotor refiner disc 11. A stator refiner disc 13 is rigidly mounted to the refiner 1, in which disc 13 the sensor probe 5 is mounted. The refiner 1 comprises a grinding gap 15 provided between the refiner discs 11, 13. The conductor body 7 exhibiting a first electric contact surface 17, which is adapted to provide electrical contact with a second electric contact surface 19, which being constituted of the grinding surface of the opposite rotor refiner disc 11, for transferring an electric current via a fiber pad material positioned in the grinding gap 15. The second electric contact surface 19 is thus formed by the rotor refiner disc 11. The first electric contact surface 17 faces away from the stator refiner disc's 13 grinding surface in a direction towards the rotor refiner disc 11. The conductor body 7 exhibits thus the first electric contact surface 17 adapted to provide electrical contact with the second electric contact surface 19 for transferring an electric current via the fiber pad material. The measuring device 3 is adapted for detecting the degree of fiber concentration of the fiber pad. The measuring device 3 further comprises a control unit 21 adapted to detect alteration of the electrical resistivity and/or conductivity of the fiber pad material by measuring the electric AC current applied through the device's 3 conductor body 7. An ampere meter 23 is connected to the control unit 21 for measurement of variations in current. The voltage of the current is constant and is fed by a power unit 25. A fiber pad having high concentration of fibers conducts the electric current poorer than a fiber pad having low concentration of fibers. The variations of resistance value of measured current through the fiber pad from the first electric surface 17 are values that are related to pre-determined fiber concentration values, which have been empirically set and being excecuted by the control unit 21. From said measured values, the control unit 21 regulates the feeding rate of fibers and the amount of added water to a mixture making the fiber pad by controlling and regulating a control valve 27 of a water supply line 29. Additionally being detected the steam point of the fiber pad being pulped, as such transformation between gaseous state and liquid state will cause a characterisitic change in resisitivity of the fiber pad.

Figure 2:
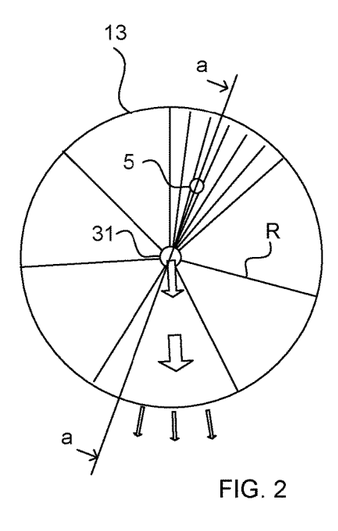
FIG. 2 illustrates a stator refiner disc comprising a sensor probe according to one aspect of the invention.

FIG. 2 illustrates a stator refiner disc 13 comprising a sensor probe 5 according to one aspect of the invention. The fibers and water are fed into the grinding gap through a centre hole 31 of the stator refiner disc 13. The sensor probe 5 is positioned two thirds of raduis measure from the centre. The steam point, i.e. the point where the water transforms from liquid state to gaseous state or vica versa, migrates backwards and forwards along the radius R during the grinding process and the sensor probe 5 detects said steam point by the detection of substantial change in electrical electrical resistivity of the fiber pad. By means of detecting the steam point position and motion there is possible to control the steam point to a desired position along the radius R, which position is determined to give the most efficient production of pulp.

Figure 3A:
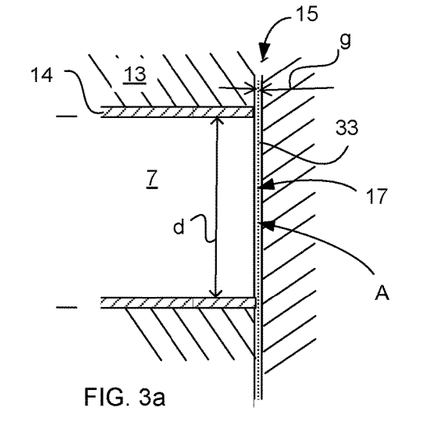
FIGS. 3a to 3b illustrates a grinding gap filled with a fiber pad having different fiber concentrations.
Figure 3B:
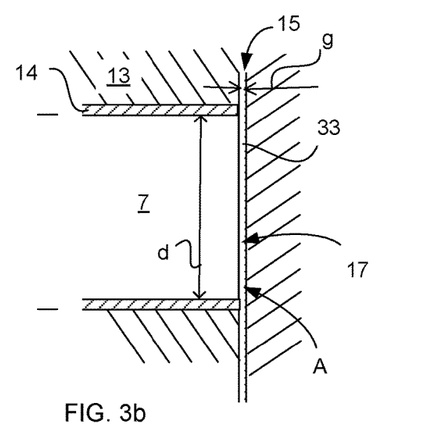

FIGS. 3a to 3b illustrate a grinding gap 15 filled with a fiber pad 33 having different fiber concentrations. In FIG. 3a there is shown a fiber pad 33 having high fiber concentration adjacent the conductor body 7 position. The position of the conductor body 7 is in this embodiment near the edge of the stator refiner disc 13. The diameter of the conductor body 7 determines the area A of the first electrical contact surface 17. The resistance is dependent upon said area A and the grinding gap 15 measure d and the resistivity of the fiber pad, which resistivity varies upon fiber content and content of water in gaseous state and liquid state respectively. In FIG. 3b there is shown a fiber pad having low fiber concentration adjacent the conductor body 7 position.

Figure 4:
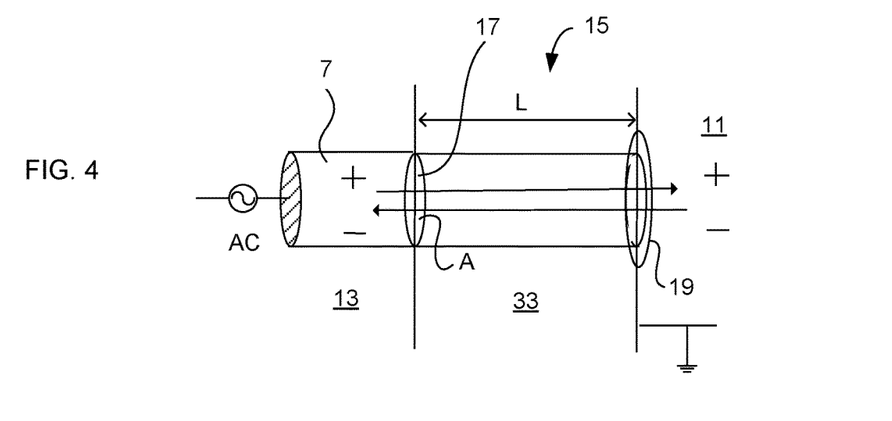
FIG. 4 illustrates the theoretical transfer of current through a fiber pad.

FIG. 4 illustrates the theoretical transfer of current through a fiber pad 33. The measure L corresponds with the grinding gap 15. This measure is known as detected by a grinding gap 15 measurement sensor (not shown). The AC current is fed from a AC power supply (not shown) to a conductor body 7 comprising a first electrical contact surface 17 having a specific pre-determined contact area A. The conductor body 7 being electrically insulated arranged within a stator refiner disc 13 so that no current overflow to the stator refiner disc 13. A second electrical contact surface 19 is provided by a surface of an opposite refiner disc (e.g. a rotor refiner disc 19). The surface 19 may be the grinding surface of the opposite refiner disc. The area of the second electrical contact surface essentially corresponds with the area A of the conductor body 7.

The area A of the first electric contact surface 17, the length L of the grinding gap 15 embodying the fiber pad 33, i.e. the distance between the refiner discs 11, 13, and the actual electrical electrical resistivity ρ of the fiber pad 33 material will determine the electrical resistance R, which being meassured continously for detecting alteration of the electrical electrical resistivity of the fiber pad 33, and thereby the actual fiber concentration and/or the position of the steam point. The formula used is $$R = \frac{\rho L}{A}$$

where R is resistance, ρ is resisitivity, L is the gap between the refiner discs and A is the area of the first electric contact surface 17.

Figure 5:
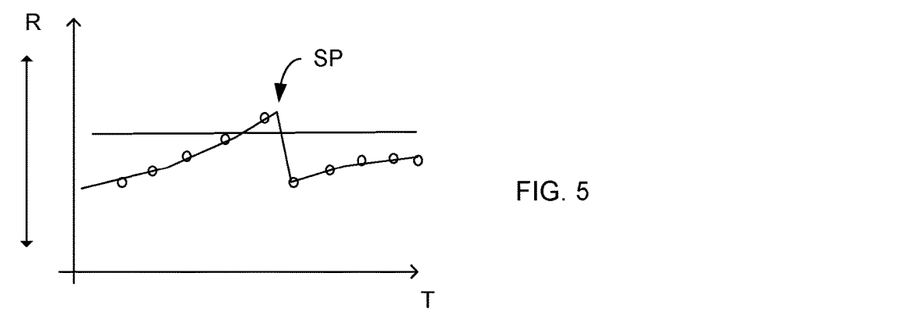
FIG. 5 illustrates a steam point profile over time.

FIG. 5 illustrates a steam point SP profile over time. At a certain resistivity of the fiber pad 33 material, the material contains a high amount of steam and the conductivity is low. By measuring the conductivity (or resistance/resistivity) there is provided a way to determine whether the fiber pad 33 is in liquid state or in a steam (gaseous) state as the gaseous state has a high resistivity relative the liquid state. The low resistivity indicates that the material readily allows movement of electric charge and thus there has been a change to liquid state (high conductivity) and vica versa.

Figure 6A:
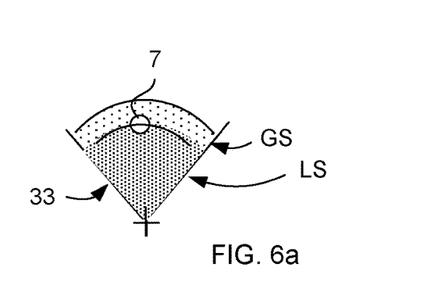
FIGS. 6a-6d illustrates variations of fiber concentration of a fiber pad.
Figure 6B:
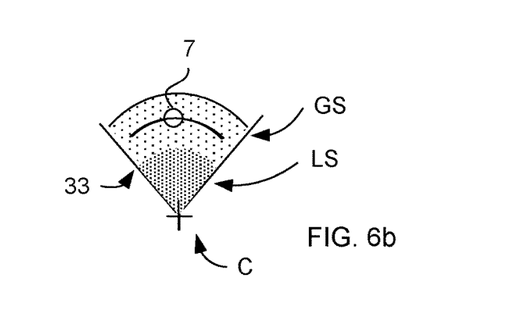
Figure 6C:
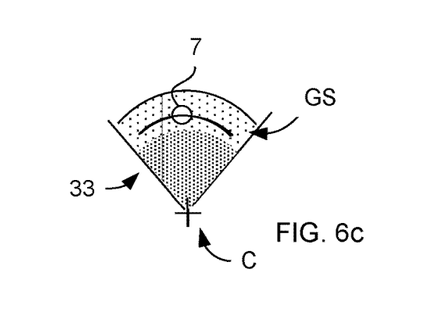
Figure 6D:
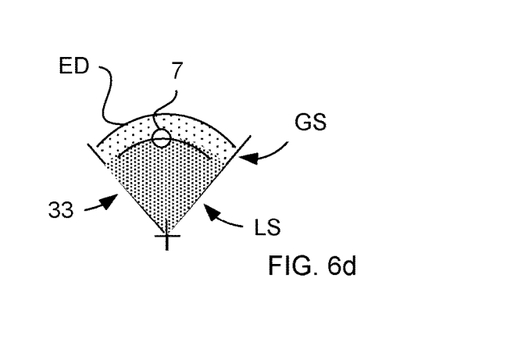

FIGS. 6a-6d illustrate variations of fiber concentration of a fiber pad 33. The FIGS. 6a-6d illustrate a section of the grinding gap between the refiner discs 11, 13. FIG. 6a illustrates that the steam point position corresponds with the position of a conductor body 7 according to one aspect. The resistivity substantially changes from high to low (liquid state LS to gaseous state GS). In FIG. 6b is illustrated that the gaseous state GS prevails and more water is added for balancing the fiber pad 33 to contain less steam as this is energy consuming. In FIG. 6c is illustrated that the steam point after such adjustment of water addition moves in radial direction outwards from the centre C and the steam point is once again detected as shown in FIG. 6d. By further addition of water, the steam point is controlled to move even further towards the edge ED of the refiner discs 11, 13 end being kept there for optimal paper pulp quality and energy saving operation of the refiner.

Figure 7:
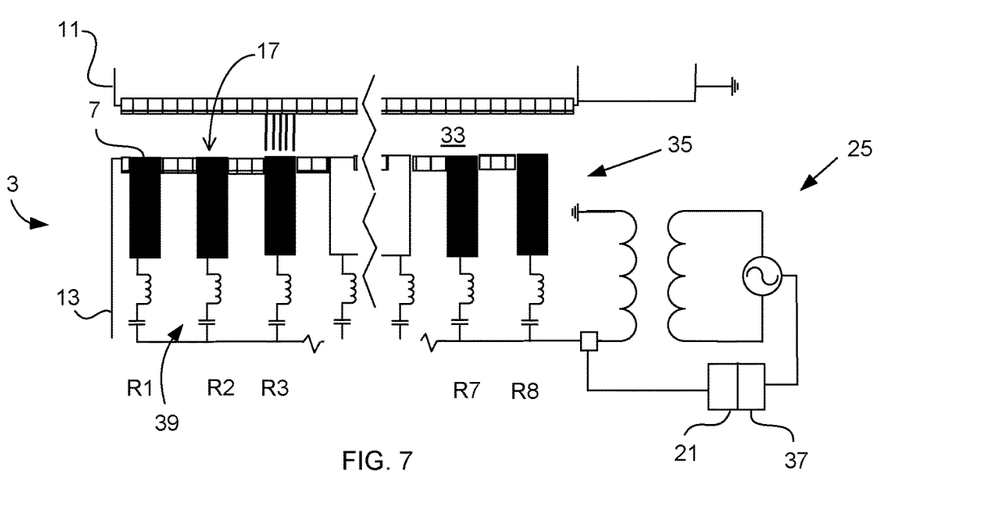
FIG. 7 illustrates a further aspect of the invention using a plurality of conductor bodies.

FIG. 7 illustrates a measuring device 3 according to one aspect of the invention. It comprises a power source 25 for feeding an AC current to a circuit 35. The power source 25 is provided with a frequency generator means 37 for generating a range of varying frequencies of the current. The measuring device 3 further comprises a control unit 21 adapted to detect alteration of the electrical resistivity and/or conductivity of the fiber pad material by measuring said electric current. The circuit 35 comprises a plurality conductor bodies 7 of a refiner disc 13, each body 7 having a certain first electrical contact surface 17 provided at a certain distance from an opposite refiner disc 11 surface. Each conductor body 7 being connected in series with a respective series resonance circuit (SRC) 39. The series connections are connected together in parallel to the power source 25. The SRCs 39 permits passage of current at one certain frequency and the other SRCs close passage of the current at said frequency. A next SRC permits passage of current at another frequency and the other SRCs closes passage of the current at such frequency. And so on, until last SRC is activated, thereafter the procedure is repeated. Each SRC 39 is thus individually adapted to give free passage to a certain frequency within said range of frequencies, wherein other frequencies hinder the current to pass. In such way an earmarking of each conductor body 7 is provided. Each earmarked conductor body 7 position along the radius R of the refiner disc 13 is thus associated with a certain frequency of the AC current. The control unit 21 is provided for for detecting which one of the conductor bodies 7 being associated with a certain resistivity of the fiber pad 33 material and thus the postion of the steam point and fiber concentration of the fiber pad 33 material.

Figure 8:
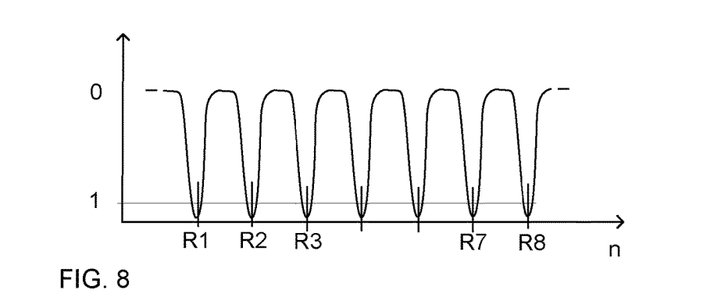
FIG. 8 illustrates a graph schematically illustrating magnitude plots.

FIG. 8 is a graph schematically illustrating magnitude plots R1, R2 . . . R8 generated by a respective conductor body 7 and SRCs 39, the positions of which are spread out over and the radius R of a refiner disc 13. FIG. 8 illustrates magnitude plots for the respective conductor body 7 being activated by the sweeing of frequency into a fiber pad concentration graph (see FIG. 9) due to the predetermined positions of the conductor bodies in the circuit.

Figure 9:
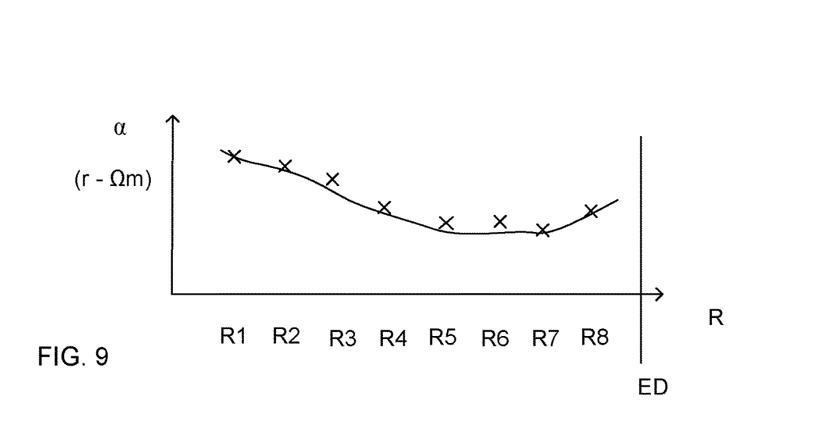
FIG. 9 illustrates a profile showing different fiber concentrations over refiner disc radius.

FIG. 9 is a profile showing the different fiber concentrations α of the fiber pad, seen in a direction from refiner disc centre towards its edge ED, i.e. over the radius R of the refiner disc.

Figure 10:
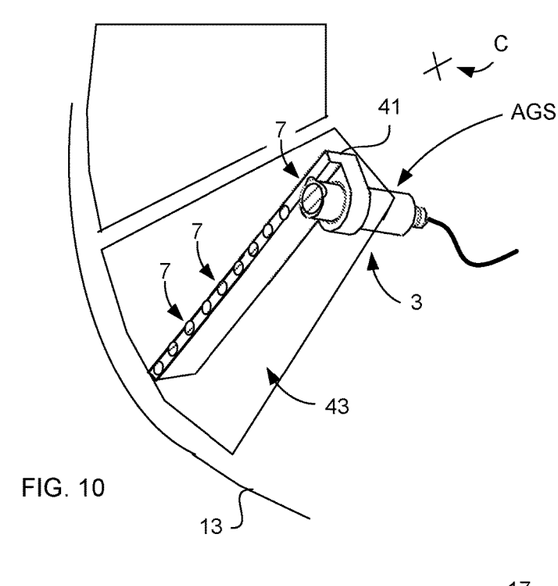
FIG. 10 illustrates a measuring device according to one aspect.

FIG. 10 shows a measuring device 3 having the conductor bodies 7 positioned side by side along a straight line in an elongated arrangement 41 (housing), wherein the first electric contact surfaces 17 of the conductor bodies 7 are coplanar with the grinding surface 43 of the refiner disc 13 in with the elongated arrangement 41 is mounted. The elongated housing encompasses an adjustable gap sensor AGS. In such way is provided a multi-functional sensor, which is adapted for cost-effective production of pulp material.

Figure 11:
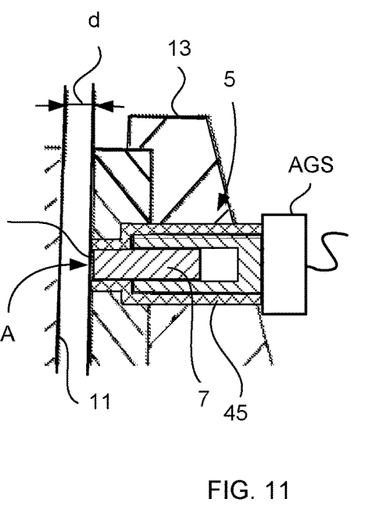
FIG. 11 illustrates a cross-section of a conductor body of a sensor probe comprising an adjustable gap sensor AGS.

FIG. 11 illustrates a cross-section of a conductor body 7 of a sensor probe 5 comprising an adjustable gap sensor AGS. The sensor per se is arranged insulated in the refiner disc by means of a rubber material 45. The first electrical surface 17 of the conductor body 7 is formed by an iron core of the AGS also used for sensing the grinding gap 15 alteration.

Figure 12:
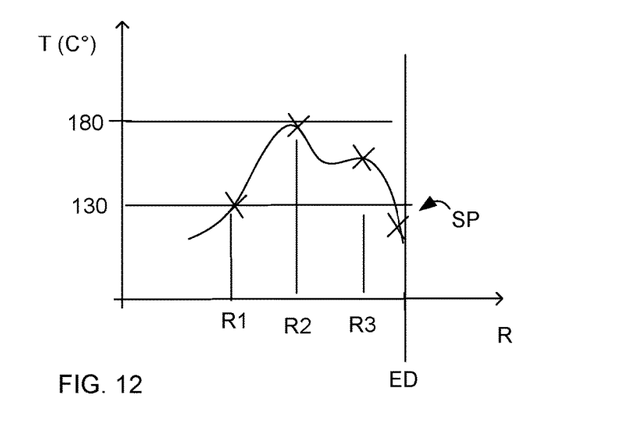
FIG. 12 illustrates a profile graph of the fiber pad material.

FIG. 12 illustrates a profile graph of the fiber pad 33 material temperature along the radius R of the refiner disc 13. The temperature is converted and derived from actual conductivity of the fiber pad 33 material. The change in resistivity over time for different positions of the radius R are parameters that are used for deriving the temperature profile. The computation of the graph is made by a control unit adapted to detect the alteration of the electrical resistivity and/or conductivity of the material 33 by measuring the resistance of the electric current flowing through the fiber pad material 33 and thereby the conductivity of the fiber pad material 33. The graph is displayed on a computer screen (not shown).

Figure 13:
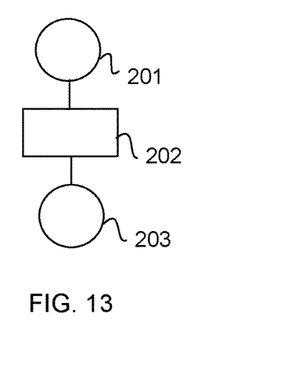
FIG. 13 is a block diagram of a method according to one aspect of the invention.

FIG. 13 is a schematic block diagram illustrating a method according to one aspect of the invention. There is shown a method for detecting, by means of a measuring device, comprising a conductor body, the degree of fiber concentration and/or stetam point of a fiber pad 33 being pulped between refiner discs forming a grinding gap 15, the conductor body 7 exhibits a first electric contact surface adapted to provide electrical contact with a second electric contact surface for transferring an electric current via the fiber pad 33 material. Step 201 recites the stop of the method. According to one aspect, step 202 comprises the steps of mounting of the conductor body 7 to one of the refiner discs 13; grinding the material 33 between the refiner discs; detecting alteration of the conductivity and/or electrical resistivity of the fiber pad 33 material; and adjusting inflow of water and/or the material from said detected alteration.

According to one aspect of the invention, the step of detecting the alteration of the conductivity and/or electrical resistivity provides the detecting of the steam point of the fiber pad 33 material.

According to one aspect of the invention, the step of detecting the alteration of the electrical resistivity is made in radial direction of the discs 11, 13.

According to one aspect of the invention, the step of detecting the alteration of the electrical resistivity is made by means of a set of conductor bodies 7, which are connected in series with a respective series resonance circuit SRC, the series connection are connected together in parallel to a power source, wherein each series resonance circuit SRC being individually adapted to give free passage for said electric current to a certain frequency.

The present invention is of course not in any way restricted to the preferred embodiments described above, but many possibilities to modifications, or combinations of the described embodiments, thereof should be apparent to a person with ordinary skill in the art without departing from the basic idea of the invention as defined in the appended claims. The fiber pad material preferably comprises cellulose fibers for making paper pulp.

The invention claimed is:

1. A fiber concentration measuring device, comprising:
a first conductor body configured to detect the degree of fiber concentration of a fiber pad being pulped, during use of the device, in a grinding gap between refiner discs of a refiner, wherein the first conductor body comprises a first electric contact surface, wherein a refiner disc grinding surface of one of the refiner discs positioned opposite the first conductor body acts as a second electric contact surface, wherein the first electric contact surface is configured to provide an electrical contact with the second electric contact surface such that an electric current is transferred via the fiber pad material;
a control unit configured to detect alteration of electrical resistivity or conductivity of the fiber pad material by measuring the electric current; and
a second conductor body, wherein the first conductor body is connected in series with a first series resonance circuit and the second conductor body is connected in series with a second series resonance circuit, wherein the first series resonance circuit and second series resonance circuit are each configured to allow passage of the electric current to a desired frequency.

2. The device according to claim 1, wherein a set of the conductor bodies are positioned side by side along a straight line in an elongated body, wherein the first electric contact surfaces of each of the set of conductor body are coplanar with the grinding surface of the refiner disc in which the elongated body is mounted.

3. The device according to claim 1, wherein the first conductor body is part of an adjustable gap sensor (AGS).

4. A method of detection comprising:
providing the device of claim 1:
mounting of the first conductor body to one of the refiner discs;
grinding the fiber pad material between the refiner discs;
detecting alteration of the conductivity and/or electrical resistivity of the fiber pad material; and
adjusting inflow of water and/or fiber material from said detected alteration.

5. The method according to claim 4, wherein the detecting of the alteration of the conductivity and/or electrical resistivity provides the detecting of the steam point (SP) of the fiber pad material.

6. The method according to claim 4, wherein the detecting of the alteration of the electrical resistivity is made in radial (R) direction of the discs.

7. The device according to claim 1, wherein a power source for providing the electric current is an AC voltage power unit for generating an AC current over a transformer comprising a secondary winding of the device.

8. The device according to claim 1, wherein a power source is provided with a frequency generator means for generating a range of varying frequencies of said electric current.

* * * * *